(12) United States Patent
Much

(10) Patent No.: US 8,017,377 B1
(45) Date of Patent: Sep. 13, 2011

(54) MASS CULTURE OF MICROALGAE FOR LIPID PRODUCTION

(75) Inventor: Alan Maxwell Much, St. Petersburg, FL (US)

(73) Assignee: AgOil International, LLC, St. Petersburg, FL (US)

( * ) Notice: Subject to any disclaimer, the term of this patent is extended or adjusted under 35 U.S.C. 154(b) by 0 days.

(21) Appl. No.: 12/174,930

(22) Filed: Jul. 17, 2008

Related U.S. Application Data

(60) Provisional application No. 61/123,982, filed on Apr. 11, 2008.

(51) Int. Cl.
*C12N 1/12* (2006.01)

(52) U.S. Cl. ............ 435/257.1; 435/802; 435/818; 435/819; 435/946

(58) Field of Classification Search ............ None
See application file for complete search history.

(56) References Cited

U.S. PATENT DOCUMENTS

| | | | | |
|---|---|---|---|---|
| 3,998,186 | A * | 12/1976 | Hodges | 119/207 |
| 4,320,594 | A * | 3/1982 | Raymond | 47/1.4 |
| 4,707,308 | A * | 11/1987 | Ryall | 261/77 |
| 5,395,006 | A * | 3/1995 | Verma | 220/371 |
| 6,105,309 | A * | 8/2000 | Takayanagi | 47/62 R |
| 6,156,561 | A | 12/2000 | Kodo et al. | |
| 6,986,323 | B2 * | 1/2006 | Ayers | 119/200 |
| 2008/0009055 | A1 | 1/2008 | Lewnard | |
| 2008/0052987 | A1 * | 3/2008 | Busch et al. | 47/62 R |

FOREIGN PATENT DOCUMENTS

| | | |
|---|---|---|
| KR | 10-0679989 B1 | 2/2007 |
| WO | 2004011659 * | 2/2004 |

OTHER PUBLICATIONS

Sheehan, J. et al., "A Look Back at the U.S. Department of Energy's Aquatic Species Program: Biodiesel from Algae", NREL National Renewable Energy Laboratory, NREL/TP-580-24190, Jul. 1998, pp. 1-328.

Yusuf Chisti, "Biodiesel from Microalgae", Science Direct, Feb. 13, 2007, vol. 25, pp. 294-306.

Aquatic Eco-Systems, Inc. Tech Talk 68 Airlift Notes. 2007 Master Catalog, p. 375.

\* cited by examiner

*Primary Examiner* — Debbie K Ware

(74) *Attorney, Agent, or Firm* — Anton J. Hopen; Smith & Hopen, P.A.

(57) ABSTRACT

A method to produce high density microalgae having high lipid concentration in mass culture including the steps of inoculating a vessel with microalgae at mid-log phase to a depth greater than 25 cm. Then culturing the microalgae to a preselected target density threshold, bringing the microalgae to stationary phase, manipulating growth parameters to maximize lipid concentration and harvesting the vessel.

17 Claims, 9 Drawing Sheets

US 8,017,377 B1

MASS CULTURE OF MICROALGAE FOR LIPID PRODUCTION

CROSS REFERENCE TO RELATED APPLICATION

This application claims priority to currently pending U.S. Provisional Patent Application No. 61/123,982, entitled "Mass Culture Microalgae Lipid Production", filed on Apr. 11, 2008, the contents of which are herein incorporated by reference.

FIELD OF INVENTION

This invention relates to the generation of lipid production from microalgae.

BACKGROUND OF THE INVENTION

The well documented damaging consequence of the widespread, long-term use of fossil fuels has resulted in a global initiative for renewable, eco-friendly alternatives. Biodiesel has been recognized as a viable solution for many reasons, such as: it is 100% renewable, because it is derived from a plant that can be grown; it can be produced from virtually any vegetable oil; it is environmentally friendly to use and process, emitting 75%-80% lower emissions than petro-diesel; it extends engine life with increased lubricity; and it offers substantially greater energy per unit.

Biodiesel is widely used in Europe, claiming 12-15% of the fuel market, and growing in the U.S., particularly in the Midwest region of the country. In Germany, biodiesel is made primarily from rapeseed oil (AKA Canola Oil), while commercial biodiesel in the U.S. is derived largely from soybean oil. The fact that rapeseed and soybeans are edible crops is a major disadvantage. Utilizing any edible crops for fuel is not a desirable solution because this results in escalating the cost of food.

A crop of rapeseed produces 127 gallons of oil per acre per year, while soybean produces only 48 gallons of oil per acre per year. Producing biodiesel from rapeseed or soybean is not cost effective, and requires government subsidies to be marketed competitively as a fuel. The soybean-based biodiesel industry in the U.S. poses little rivalry to the petroleum industry. In most cases, biodiesel is dispensed as a 10% or 20% additive (B10 or B20) to petro-diesel, co-existing comfortably with the dominant fuel.

Another source of oil for biodiesel that is garnering increased interest is a plant called *Jatropha curcus*. Unlike soybean or rapeseed, Jatropha is a perennial plant which produces large oil-rich seeds beginning in the fourth or fifth year of growth. Annual production of jatropha oil per acre has been documented at a notable 202 gallons, considerably higher than rapeseed (127 gals.) or soybean (48 gals.). Jatropha is non-edible, a trait that increases its viability as a potential solution for a fuel crop. The plant is, however, cold-sensitive, and grows only in tropical and semi-tropical locations, which markedly limits its pervasiveness. Jatropha plantations aimed at biodiesel production are quickly increasing in India, Philippines, Vietnam, and several African countries.

Some species of microalgae are inherently comprised of 50% oil. Algae are the most densely growing plants on earth, yielding more per acre than any other crop. When growth factors are optimal, they can double their weight within hours. Estimates of per-acre annual yields range as high as 20,000 gallons. Even conservative estimates project yields starting at 3,600 gallons per acre per year. In comparison with other sources of oil for biodiesel, the potential of microalgae is unsurpassed.

A variety of algae species have been grown for decades as feed for aquaculture, nutritional supplements, pharmaceutical applications, and cosmetic ingredients. They are a source of pigments, proteins, enzymes, vitamins, and amino acids.

Microalgae are grown with inexpensive raw materials—sunlight, water, carbon dioxide, and horticultural nutrients—and without pesticides or herbicides. They are relatively simple to process with today's technologies.

There has been an abundance of recent publicity, along with scientific consensus,
[Technology Review, Published by MIT, Feb. 5, 2007, "Algae-Based Fuels Set to Bloom."] that growing algae in mass culture as an alternative fuel oil source is not only viable, but possibly the best solution proposed thus far. "On a commercial scale, the economic production of biodiesel using algae is simply a no-brainer." This statement by Nick Hodge, editor of the Green Chip Review investor's publication, echoes a widely-accepted viewpoint.

Since algae have such salient advantages as a source of oil for biodiesel, why hasn't this crop already materialized as the premier solution for today's alternative fuel dilemma? The answer is simple. Although significant effort has been expended over the past thirty years, reliable cost effective methodologies for growing high-lipid microalgae in mass culture have yet to be established. There is a long-felt but heretofore unfulfilled need for commercial production of biodiesel from algae oil in the marketplace.

The DOE Aquatic Species Program: Biodiesel from Algae

The U.S. Department of Energy (DOE) began an extensive investigation of algae as a source of biofuel oil thirty years ago. From 1978 to 1996, the U.S. Department of Energy's Office of Fuels Development funded a program to develop renewable transportation fuels from algae. The main focus of the program, known as the Aquatic Species Program (ASP) was "the production of biodiesel from high lipid-content algae grown in ponds, . . ." This statement was taken from the Executive Summary of the landmark document entitled "A Look Back at the U.S. Department of Energy's Aquatic Species Program: Biodiesel from Algae, Closeout Report", published in July of 1998.

A summation of the NREL vision from page 10 of the report is noted as FIG. 1 Prior Art. On an algae farm, this single pond would be duplicated repeatedly, as space and resources allow. After nearly two decades of research and an expenditure of more than $450M, much was revealed about hundreds of algae species that exhibited high concentrations of oil. Large-scale open ponds were built for mass culture, but according to the report, "Attempts to achieve consistently high productivities were hampered by low temperature conditions encountered at the site." In spite of the fact that their system design did not deliver consistently high productivity, the NREL study repeatedly asserted, "A major conclusion from these analyses is that there is little prospect for any alternatives to the open pond designs . . ." and "Several decades of R&D in this field . . . have revealed no plausible alternative to this basic design" which is described as "large unlined, open, mixed raceway ponds." NREL concluded that "The commercial experience with open mass culture ponds suggests that such systems require relatively little further engineering development."

In lieu of seeking culturing methods that permitted control of parameters to optimize the culture of extant organisms, the NREL report proposed that the solution to achieving consistently high productivity of mass culture of algae lies in the genetic engineering of new strains of microalgae that would perform ideally in the recommended open pond systems.

The 300-page document that emerged from this two-decade study became recognized as the authoritative manual on the topic of 'Biodiesel from Algae.' Many subsequent researchers followed the guidelines set forth in the NREL study. Companies continue to propose the production of oil from algae for biodiesel using huge open ponds and seeking genetically engineered strains.

Although the DOE's NREL algae research project terminated in 1996 due to curtailed funding, their efforts to produce biofuel from algae oil were revived in 2007 through a collaborative agreement with Chevron Oil Company. "Chevron and NREL scientists will collaborate to identify and develop algae strains that can be economically harvested and processed into finished transportation fuels . . . ."

Skepticism and negativism were lasting effects of the absence of consistent results from the NREL study. In 2007 one energy columnist wrote on the Biopact website, "Most of the algae companies have never proved that the technology works on a continuous basis and/or on a large scale." "Open ponds were seen as the only viable option, but came with many drawbacks (such as contamination with rival organisms and pollution)." "Since the discontinuation of most algae-biofuel research in the 1990s, there have been no major biotech breakthroughs in the field."

SUMMARY OF INVENTION

This patent application presents a new direction for the mass culture of algae that is diametrically opposed to the prevailing trend of the last decade—a new direction that is simple, direct, logical, environmentally-beneficial, relatively inexpensive, and incorporates key findings of recent laboratory research relative to the optimization of high-lipid production in microalgae.

The invention includes a method to produce high density microalgae having high lipid concentration in mass culture. Steps to the method include inoculating a vessel with microalgae at mid-log phase, culturing the microalgae to a preselected target density threshold, bringing the microalgae to stationary phase, manipulating growth parameters to maximize lipid concentration and harvesting the vessel.

The vessel may have a depth greater than 25 centimeters due to airlift pumps that provide multidirectional circulation that brings algae sufficiently near the surface of the solution to sustain growth. In a preferred embodiment, a translucent contamination barrier covers the vessel and the vessel is thermally insulated.

To maintain proper temperature, a heat exchanger is submerged in the vessel to control temperature. If the heat exchanger is constructed of a corrodible material such as copper, the heat exchanger is enveloped in a polymer-based, fluid impermeable sleeve thereby precluding contamination of the culture and corrosion of the heat exchanger. Alternatively, the heat exchanger comprises substantially corrosion-resistant polymer tubing in a predetermined serpentine configuration. The heat exchanger substantially longitudinally bifurcates the vessel and a plurality of directional air lift pumps are affixed to the heat exchanger.

The directional air lift pumps are oriented to simultaneously create an uplift current from the bottom of the vessel to the top of the vessel and a rotational current defined by the perimeter of the vessel as the outer boundary and the heat exchanger as the inner axis.

The exhaustion of a specific nutrient induces initiation of the stationary phase of the culture. With deference to the organism being cultured, relative lipid concentrations are increased during the stationary phase by manipulation of nutrient levels and/or growth factors. Carbon dioxide is introduced into the culture by airlift pumps.

Algae require light to grow and continuous lighting optimizes growth potential. Accordingly, an embodiment of the invention exposes the algae in the vessel to artificial lighting at wavelengths between 450 and 475 nm and 530 to 675 nm. The lighting may be from any suitable source. However, metal halide lights, high pressure sodium lights and LED lights may be employed in efficient embodiments of the invention.

As the algae respond primarily to certain wavelengths, extraneous wavelengths may only serve to heat the vessel and require additional cooling of the solution. To enhance efficiency, an embodiment of the invention selectively filters out ambient light to preselected wavelengths required for algae growth thereby reducing heat absorbed by the culture in the vessel. A heat barrier may also be suspended over the vessel wherein the heat barrier shades the culture.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
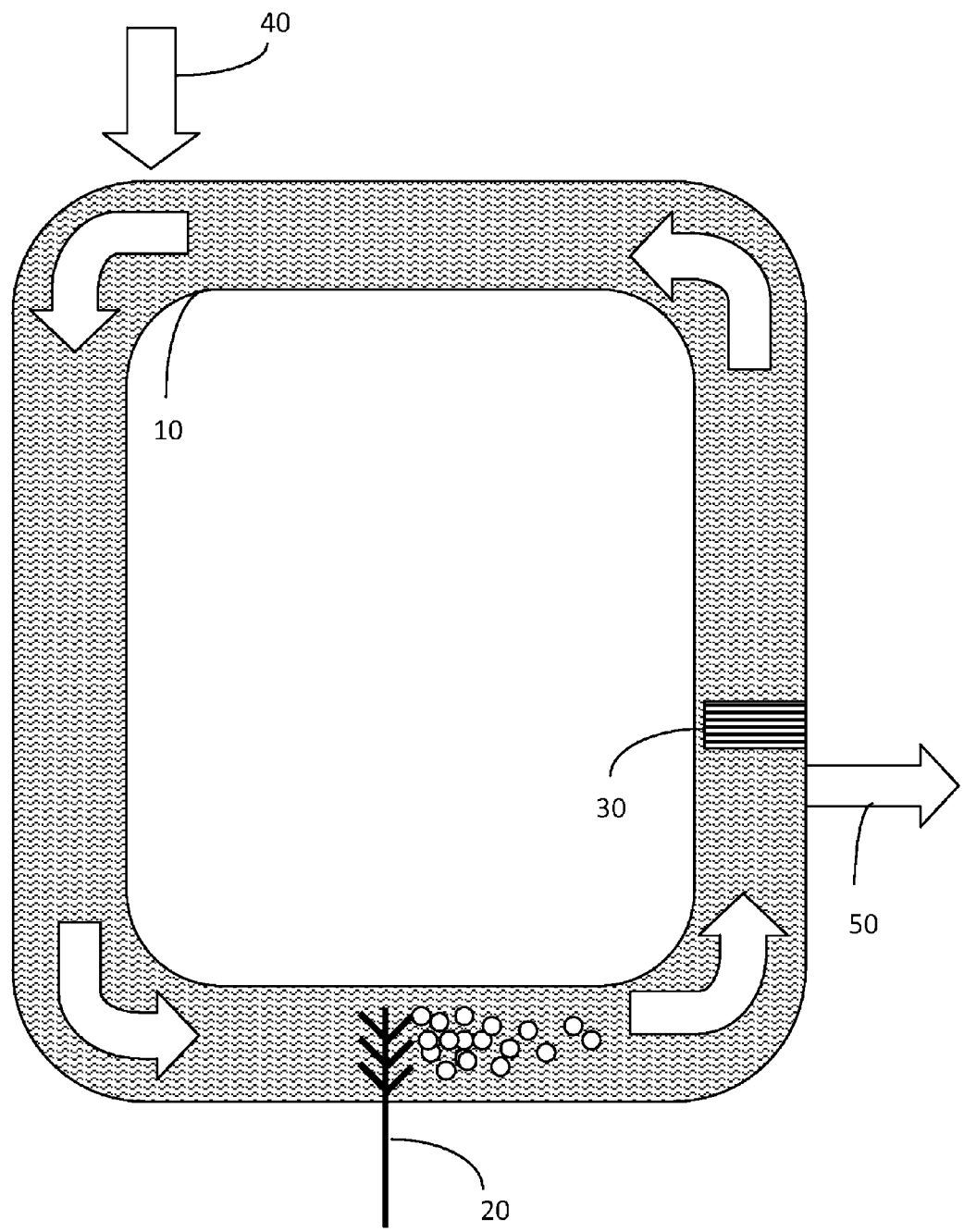
FIG. 1 is a diagrammatic view of a prior art method.

A guiding principle throughout the design of this system is cost effectiveness. The equipment and supplies utilized are readily available from farm and commercial warehouses rather than from more costly scientific or laboratory sources or custom fabrication. In addition, many of the techniques and procedures employed represent a synthesized re-purposing of elements and components of existing procedures and processes. These basic guidelines of utilizing inexpensive, available components from a wide range of disciplines, and re-channeling their applications, results in practicality and cost effectiveness.

The unique system is based on two fundamental concepts that are not employed in other microalgal culturing systems:
1) Exploiting the High-Density Stationary Phase of Microalgal Growth.

The phenomenon of the algal bloom that occurs in nature creates microalgal outcroppings so dense that they can be seen from space. There are more than 100,000 different species of microalgae. While some species produce toxic blooms that may constitute health hazards for both humans and animals (e.g. red tide), other species produce blooms that serve as vast reservoirs of food for small aquatic animals (zooplankton), which are, in turn, eaten by larger organisms, thus initiating the food chain of life on our planet.

In algal culture, the highest concentration of growth is reached during the stationary phase. In huge raceways, built for continuous harvesting, if stationary phase were reached, the culture would 'crash' (die), due to rapid depletion of nutrients, oxygen deficiency, overheating, and/or pH disturbance. For this reason, the phenomenon of the algal bloom, as seen in nature, has not been intentionally simulated as a method of commercial culture of microalgae. In cases where stationary phase has occurred unintentionally in continuous production systems, results were disastrous, requiring complete shutdown, cleanout, and beginning anew.

Fundamental issues regarding algae growth are found in the *Handbook of Microalgal Culture, Biotechnology and Applied Phycology*, A. Richmond, editor, Blackwell, Oxford, 2004 and *Algae, Anatomy, Biochemistry, and Biotechnology*, Barsanti, Laura and Paolo Gualtieri, CRC/Taylor & Francis, 2006. Both citations are incorporated herein by reference.

The system is designed to optimize the culture in the harvesting tanks until it reaches stationary phase, followed by the maximization of oil production. Then the tank is harvested.
2) Controlling the Parameters of Microalgal Growth in Mass Culture.

Optimized mass culture of microalgae can be achieved repeatedly if, and only if, all growth factors are closely controlled. The regulated conditions of indoor laboratory culture must be reproduced in outdoor vessels. The factors to be controlled are:

| | |
|---|---|
| Temperature | Salinity |
| Light | Mixing/Circulation |
| pH | Contamination |
| Nutrients | Predators |

While optimizing growth parameters is essential for consistent production of the culture of the organism, it is also essential to achieve maximum production of oil, which is the ultimate objective. Capitalizing on lipid research, which has abounded in recent years, also requires full control over all growth parameters.

The shallow, open raceway design recommended by NREL and similar large open pond systems cannot be adapted to the requisite control of parameters. Their vast open designs utilize sunlight, provide a mechanism for circulation, and incorporate nutrients, but other key parameters, such as temperature control and prevention of contamination are not possible. Therefore, parameters of growth cannot be optimized in multi-acre ponds or raceways.

When growth factors are controlled, the benefits of laboratory research can be fully realized in mass culture. For example, research has shown that the quantity of lipids produced can be manipulated by adjusting nutrient levels at certain phases of growth. The NREL culturing systems could not take advantage of "lipid productivity data". They admitted that "the process for maximizing lipid yields from microalgae grown in mass culture never was optimized. Therefore, there was no basis for designing experiments to estimate lipid productivity potential." If the benefits of laboratory findings could not be utilized in their system of mass culture, then competitiveness would be precluded.

Key Functions and Features
Indoor-Outdoor System
The present inventive method initiates with inoculum grown indoors in a 400 gal tank that is a scaled-down model of larger outdoor tanks.

Built-in Multi-Function Parameter Controls
Each growth factor controlling device serves more than one function and is simple to install.

Sequential Batch Harvesting
The final stage of the inventive method employs a deep 8,000 gallon tank in which the culture is grown to stationary phase, oil production is maximized, and then the culture is harvested.

Cost Effectiveness
Simplicity of operation, minimization of energy consumption, and readily available inexpensive components characterize the system throughout.

Water Source
The abundance of salt water in coastal areas and bays makes it the preferred source. Unlike microalgal cultures intended for aquaculture feeds or human consumption, algal oil produced for fuel can make use of contaminated water. Under these circumstances, remediation of contaminated waters represents a significant value-added objective.

Organism
A number of different marine microalgae offer high-lipid potential, and their culture requirements have been well documented.

The Culture Tanks and Inoculum Sequence
Published data from laboratory research implies that more extensive exploitation of algae can be achieved by devising a two-phase system where inoculum is produced indoors under laboratory conditions and mass culture is carried out in outdoor vessels. This model has been adopted, with identical control systems installed in the indoor and outdoor tanks.

Preparation of inoculum is achieved by standard laboratory methods of inoculum buildup for microalgae in continuous culture tanks. The unique parameter control system developed herein begins in the inoculum tanks, which are grown to exponential growth phase (FIG. 3, Stage II), while the final 8,000 gal harvest tanks are grown to stationary phase. A full explanation of each phase in the growth curve has been documented in many publications (see for example, FAO Fisheries Technical Paper No. 361, "Manual on the Production and Use of Live Food for Aquaculture," Lavens, P. and Sorgeloos, P. 1996, pp. 23-24, or any standard reference on microbial culture).

Closely monitoring the growth phases of the culture is essential. This is achieved through frequent periodic optical density readings of the culture, which can be automated. There is a close correlation between cell number and optical density. Inoculation tanks are transferred during exponential phase (mid-log) when the organism reaches highest rate of reproduction. Maximum lipid concentration has been observed to occur in stationary phase, when final product is harvested.

Tank Design and Control Systems
To maintain optimal culture conditions and to take full advantage of results of ongoing laboratory research, all growth factors are controlled and monitored. The functionality in the smaller indoor tank(s) is a miniature of the larger outdoor tanks; that is, all tanks have the same mechanisms for controlling parameters, differing only in dimension.

This section describes how the control of parameters is achieved in the culture tanks.

Cover—All tanks PhycoMax System Unit are fitted with a clear plastic cover. While exposing the culture to sunlight in the outdoor tanks, the cover prevents dilution by rain, provides protection from the elements, reduces risk of contamination and invasion by predators, provides a means of filtering light and applying shade, if necessary, prevents escape of injected carbon dioxide, and serves as a one-way valve to release oxygen.

Insulation—A layer of expanded polystyrene thermal insulation covers sides and bottom of each tank.

Liner—A tank liner is inserted into each tank before filling. A clean liner eliminates the task of cleaning the tank after each batch and minimizes contamination.

Lighting—All culture tanks receive 24 hours of illumination. Artificial lighting is provided when sunlight is unavailable. Research has shown that intensity of lighting is a factor in increasing oil production in the stationary phase.

Center Divider—To achieve a continuous circulatory flow and mixing within each tank, a center divider is required. Multiple functions are incorporated into the center divider of each tank: manifold for distribution of air and $CO_2$, support for Air Water Lift (AWL) pumps, and heat exchanger unit.

Mixing, Circulation—Mixing and circulation are required to prevent sedimentation and to ensure uniform exposure of the population to the light.

Air-Water Lift (AWL) Pumps are key components that provide several essential functions while using very low energy. AWLs are inexpensive components, made from plastic pipe. They have been in use for several decades in the aquaculture industry. A bank of AWLs, attached to each side of the center manifold, serves multiple functions in the tanks. Injection of continuous aeration is economically supplied by a single air pump to multiple tanks.

$CO_2$ and pH—The air line tube serves a dual function. $CO_2$ injection is merged into the air delivery. Injection of $CO_2$ is released as needed, determined by pH sensor and supplied by a single source of $CO_2$ for multiple tanks. As an autotrophic organism grows (divides) in the culture, it consumes $CO_2$ dissolved in the media and, as a result, the pH rises. The pH range for most cultured algal species is between 7 and 9, with the optimum range being 8.2-8.7. A programmed logic controller (PLC) monitors the pH, and when a pre-determined level is reached, $CO_2$ is released into the manifold.

$CO_2$ is a requirement for algal growth. It should be noted that for every ton of algae grown, 2.2 tons of $CO_2$ are consumed. This statistic highlights the outstanding potential of our algae farms as agents for recycling of sequestered $CO_2$ emissions.

Mixing of nutrients to maintain uniformity of the culture.

The AWLs provide directional flow to the tank as media is expelled. They pull the bottom layers of the culture up to the top for exposure to the light. The light penetrates only a few inches into a static culture, and as the top layer grows and consequently increases in density, lower layers are shielded from the light. The depth of the tanks requires continuous vertical lifting in addition to lateral circulation.

Temperature/Heat Exchanger

The optimal temperature for microalgal cultures ranges between 20 and 24° C., while temperatures from 16 to 27° C. are tolerated. Temperatures lower than 16° C. will slow down growth, whereas those higher than 35° C. are usually lethal for most species. Research has shown a relationship between temperature change and oil production, underscoring the requirement for temperature control, particularly in the stationary phase.

To maintain optimal temperature, a simple heat exchanger is constructed from tubing with high heat transfer properties, such as copper. A bank of serpentine tubing, sized to fit the height and length of the tank, is encased in a sealed plastic envelope and affixed. The plastic envelope prevents the tubing from being in direct contact with the salt water media. Water circulating in the tubing is heated or cooled via a heat pump. A PLC determines the temperature of the reservoir. One heat pump serves multiple vessels.

An alternative embodiment to the copper medium is to use polyethylene (e.g., pex) tubing. The non-corroding properties of the polymer tubing obviate the necessity of the sealed plastic envelope. Another advantage of the polymer tubing is the reduction of expense compared with other materials such as copper.

Nutrients—The recommended nutrient balance varies depending on the organism being grown. Appropriate culture media are well documented for each organism.

The quantity of the nutrients directly affects the density of the population. The manipulation of nutrients in the stationary phase affects the level of oil production. Strategies for management of nutrients is different in the inoculum tanks, when reproduction is rapid, versus the harvest tanks, where the culture is brought to targeted density, becomes static, and oil production can then be stimulated.

Harvest Tanks—Surplus cargo shipping containers were selected for this function, in compatibility with guidelines for cost effectiveness and availability of components. The structural integrity and durability of the containers are indisputable.

Doors are welded closed, sealing all openings. The routine use of tank liners precludes concerns over watertight condition of the container.

The size of the container is 8' wide by 40' long by 9½' deep. The 40' (12.2 m) containers are the most frequently used cargo containers and most widely available in surplus. Cutting two of these containers in half lengthwise yields 4 tanks, that are each 4½ ft. deep. Filling to a depth of 3.5° to 4' provides approximately 8,000 gal of volume and allows ample space at the top to fit the center divider-manifold and leave a rim. The depth of the NREL raceway design was approximately 1 ft, kept intentionally shallow to enable penetration of sunlight. This necessitated a very large footprint. In contrast, the harvest tanks holds 3.5 to 4 feet of media, enabling far greater yields with much smaller footprint, due to the ability of the ultra-efficient AWLs to continually lift the lower layers up into the light.

Turning now to the drawings, FIG. 1 illustrates the prior art. Algae farms according to the current state of the art are prescribed to be an open, shallow pond raceway 10. Waste carbon dioxide 20 is bubbled into the ponds to be consumed by the algae. Raceway 10 circulates algae, water and nutrients by paddlewheels 30. Raceway 10 is kept shallow because of the need to keep the algae exposed to sunlight and the limited depth to which sunlight can penetrate the pond water. Raceway 10 is operated continuously; that is, water and nutrients 40 are constantly fed to raceway 10, while water-containing algae is removed 50 at the other end. A harvesting system is required to recover the algae which contain amounts of natural oil.

Figure 2:
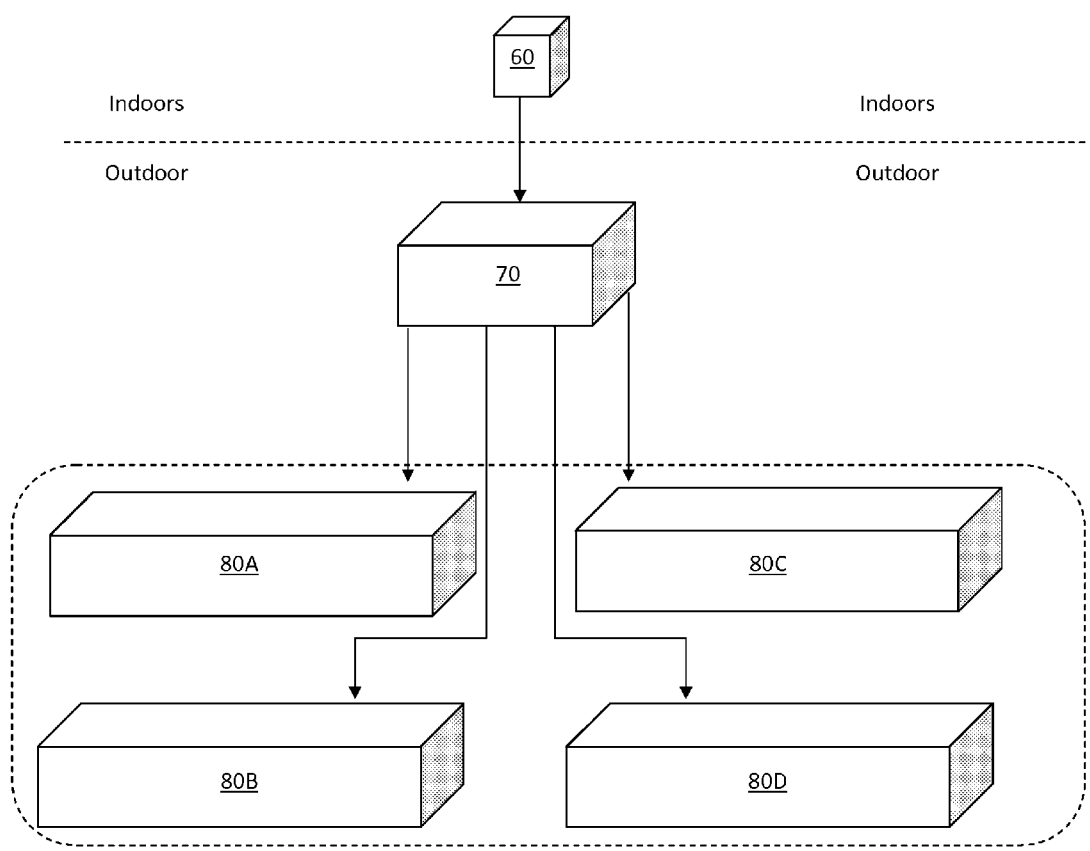
FIG. 2 is a diagrammatic view of an embodiment of the current invention showing inoculum vessels introduced into larger harvest tanks.

FIG. 2 illustrates an embodiment of the invention wherein tank of algae is brought to mid-log phase in a controlled indoor environment. Container 60 is then used as a ten percent (10%) inoculum for a larger container 70 which is maintained outside, but still within specific control parameters. Container 70 is then brought to mid-log phase and serves as continuous inoculum (10%) for 8,000 gallon harvest tanks 80A-D. Harvest tanks 80A-D are subsequently brought to stationary phase. Conditions are manipulated to lipid concentration. When a predetermined lipid concentration has been achieved, containers 80A-D are completely emptied (harvested), washed and put back online to receive more inoculum from container 70.

The present invention is counter-intuitive to the teachings of the prior art's continuous raceway 10. Rather than using a continuous system, the present invention discloses a plurality of stages wherein the vessel holding the algae is completely emptied once a predetermined threshold is met. A unique advantage of this stepped approach is that contamination of one vessel can be quickly and efficiency controlled. In contradistinction, if raceway 10 is contaminated, the entire volume of algae must be discarded and raceway 10 cleaned.

Figure 3:
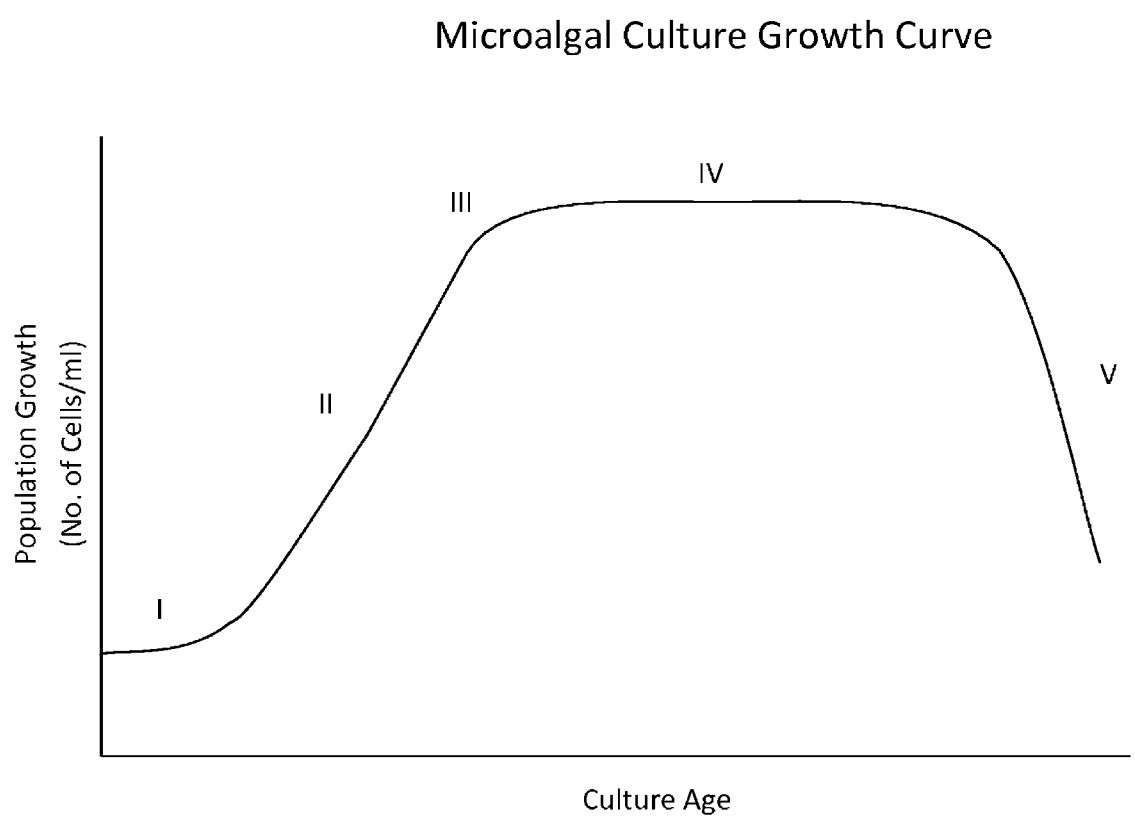
FIG. 3 is a microalgal culture growth curve.

FIG. 3 illustrates a microalgal culture growth curve wherein Stage I represents the lag or starting phase. Stage II represents the exponential phase. Stage III represents the declining growth phase. Stage IV represents the stationary phase. Stage V represents the death phase or "crash."

Figure 4:
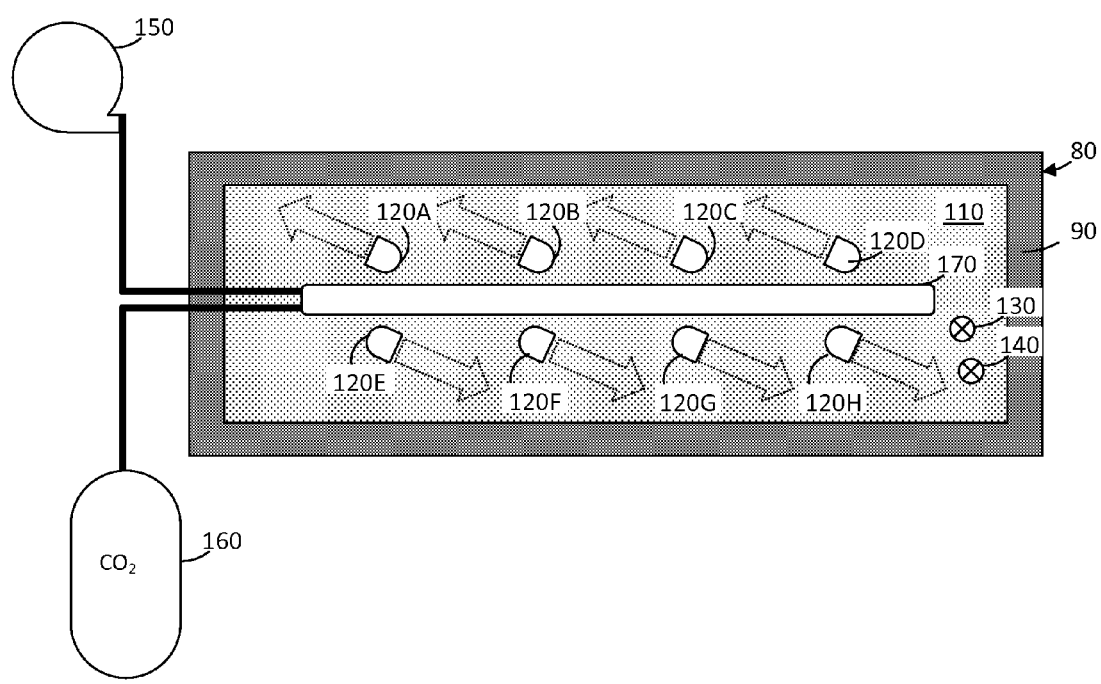
FIG. 4 is a partially sectional, overhead view of an embodiment of the current invention showing an exemplary tank design.

In FIG. 4, an overhead view of container 80 is provided. It is anticipated that container 80 will constitute a standard shipping container cut longitudinally. Thermal insulation 90 is sandwiched between the outer wall of container 80 and fluid impermeable inner wall 100. Inner volume 110 defines the interstitial space holding algae solution circulated by airlift pumps 120A-H. Temperature sensor 130 and pH sensor 140 provide data to control the operating parameters. Air supply 150 and carbon dioxide supply 160 flow through air manifold 170 which is fluidly coupled to airlift pumps 120A-H. Directional arrows show a generated current.

Figure 5:
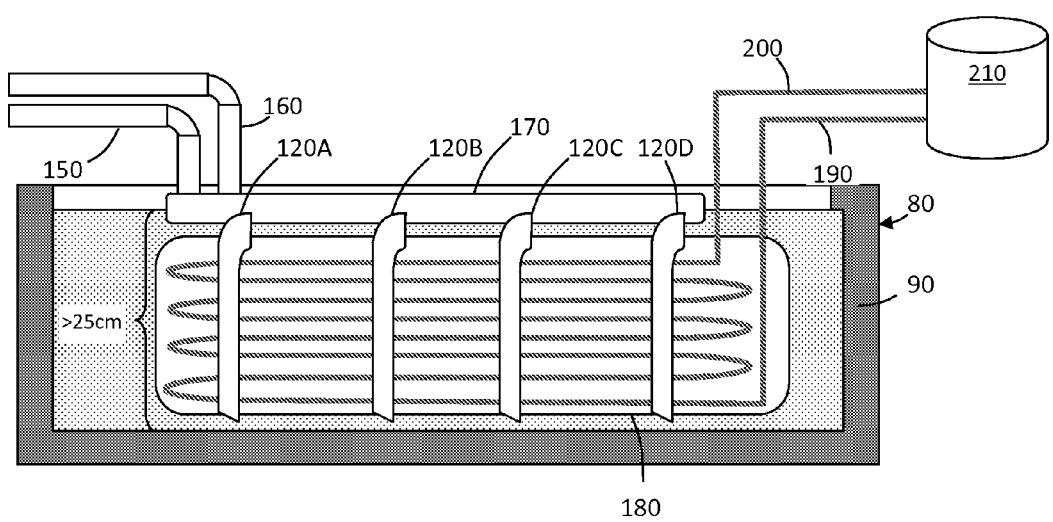
FIG. 5 is a partially sectional, elevated view of an embodiment of the current invention showing an exemplary tank design.

In FIG. 5, an elevated view of container 80 is provided. Airlift pumps 120A-D are longitudinally spaced and fluidly coupled to air manifold 170. Disposed between airlift pumps 120A-D and airlift pumps 120E-H is heat exchanger 180 fed by intake conduit 190 coupled to temperature control reservoir 210. Discharge conduit fluidly couples heat exchanger 180 to reservoir 210. Multiple embodiments of heat exchanger 180 may be deployed. Metallic tubing may be used to circulate fluid for temperature control. One concern of metallic tubing such as copper is corrosion, particularly in saline solutions. Accordingly, it is anticipated that metallic tubing may be enveloped in a fluid-impermeable but thermally conductive polymer sleeve. Another embodiment of heat exchanger 180 is polymer tubing which obviates the need for the protective sleeve and may considerably reduce the material costs for heat exchanger 180.

Figure 6A:
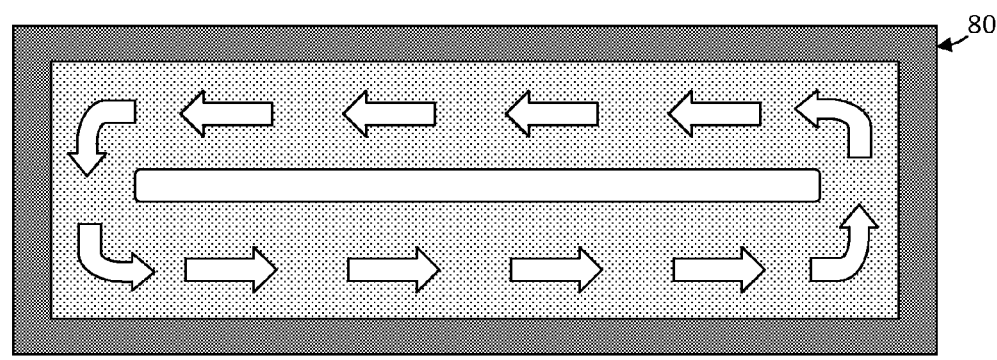
FIGS. 6A-6B are partially sectional views of an embodiment of the current invention showing current flow in an exemplary tank design.
Figure 6B:
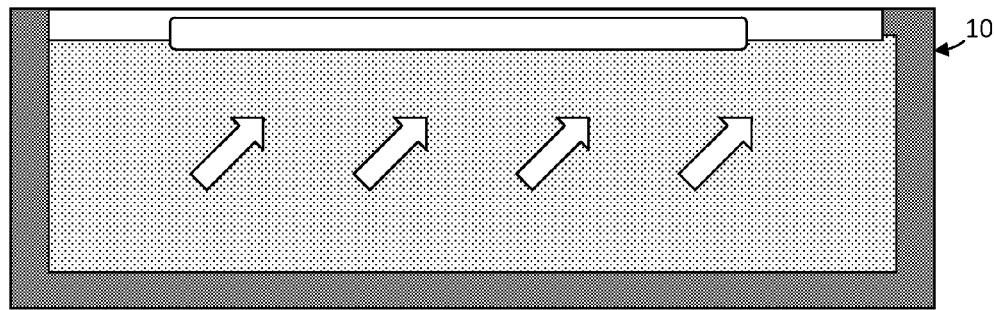

FIGS. 6A-6B illustrate optimum circulation of algae within container 80. In FIG. 6A, an overhead view shows circulation about a horizontally elongate axis defined by air manifold 170. However, this lateral circulation is insufficient alone bring all the algae shallow enough for optimum growth. Vertical circulation is also required. Accordingly, FIG. 6B shows a simultaneous upward circulation in container 80. This multidirectional circulation is achieved via airlift pump 120 as shown in FIG. 7.

Figure 7:
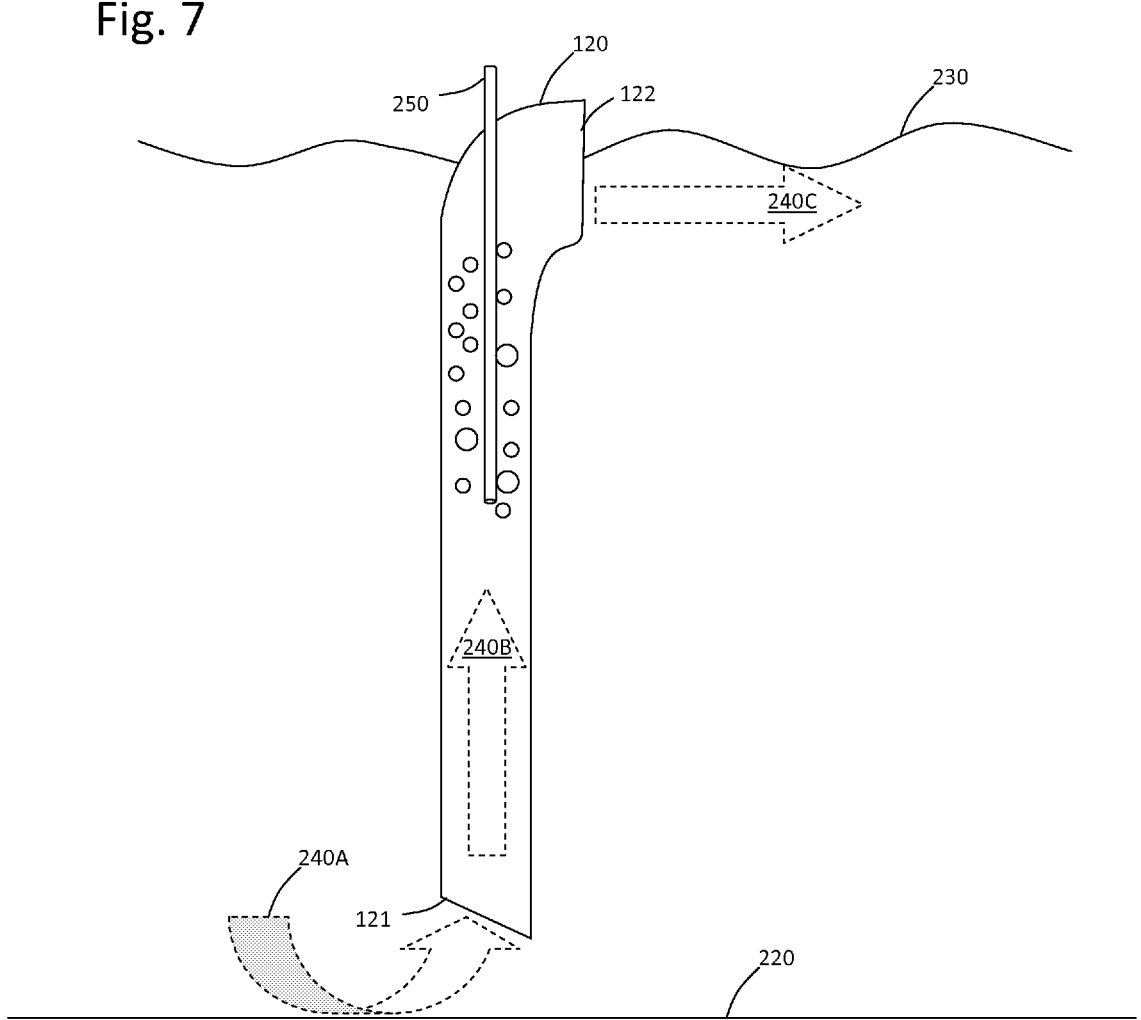
FIG. 7 is a partially sectional, elevated view of a water air lift system.

In FIG. 7, airlift pump 120 is defined by lower aperture 121 angled to a first direction and upper aperture 122 angled in an opposite direction. Airlift pump 120 conducts fluid through fluid path 240A-C from container bottom 220 to water level 230. Air line 250 injects gas 260 only partially down length of airlift pump 120 causing a lower-pressure area to generate fluid path 240A-C.

Figure 8:
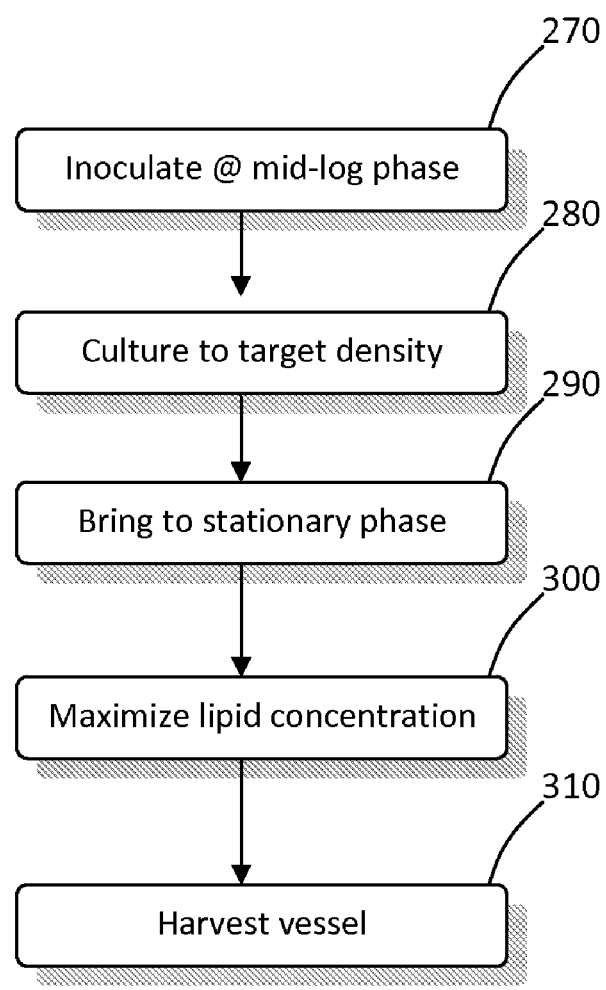
FIG. 8 is a diagrammatic view of steps according to an embodiment of the invention.

In FIG. 8, steps to the invention include, inoculating vessels at mid-log phase 270, culturing to a target density 280, bringing the medium to stationary phase 290, maximizing lipid concentration 300, and harvesting the vessel for the lipids 310.

Figure 9:
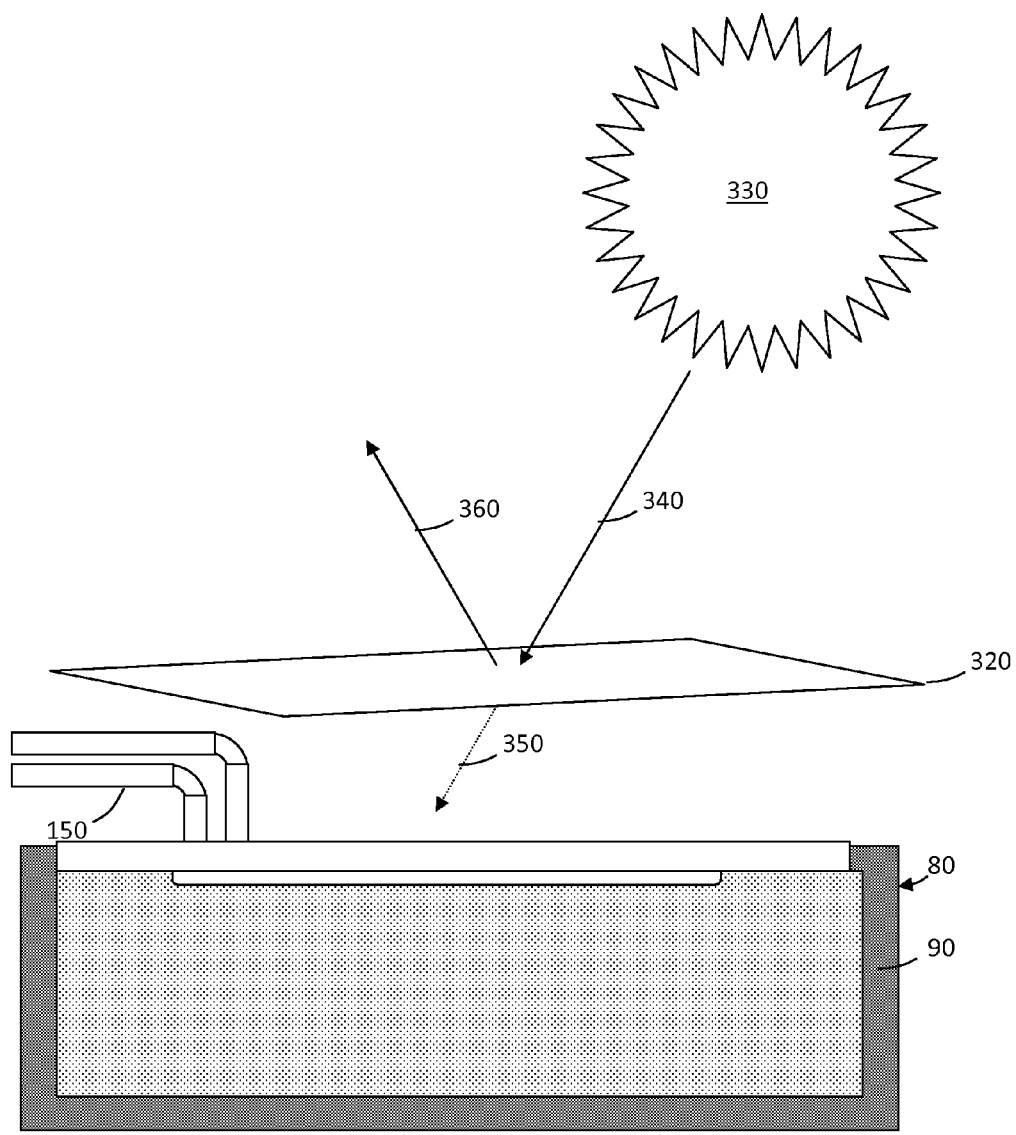
FIG. 9 is a partially section, elevated view of an embodiment of the invention illustrating a partially reflective heat barrier.

In FIG. 9, ambient light 330 is selectively filtered by heat barrier 320. Full-spectrum light 340 meets heat barrier 320 which passes light wavelengths 350 compatible with high algae growth and reflects unwanted wavelengths 360 thereby reducing temperature within container 80.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described, What is claimed is:

1. A method to produce high density microalgae having high lipid concentration in mass culture comprising the steps of:
   inoculating and covering a vessel with an inoculant comprising microalgae at mid-log phase to a depth greater than 25 centimeters;
   providing a heat exchanger submerged in the vessel to control temperature;
   providing a plurality of directional air lift pumps inside of the vessel whereby the directional air lift pumps are oriented to simultaneously create an uplift current from the bottom of the vessel to the top of the vessel and a rotational current defined by the perimeter of the vessel as the outer boundary;
   culturing the microalgae to a preselected target density threshold;
   bringing the microalgae to stationary phase;
   manipulating growth parameters selected from the group consisting of temperature, light, pH, nutrients, and salinity during stationary phase to maximize lipid concentration; and
   harvesting the microalgal culture from the vessel.

2. The method of claim 1 wherein a translucent contamination barrier covers the vessel.

3. The method of claim 1 wherein the vessel is thermally insulated.

4. The method of claim 1 wherein the heat exchanger is enveloped in a polymer-based, fluid impermeable sleeve thereby precluding contamination of the culture and corrosion of the heat exchanger.

5. The method of claim 1 wherein the heat exchanger comprises corrosion-resistant polymer tubing in a predetermined serpentine configuration.

6. The method of claim 1 wherein the heat exchanger longitudinally bifurcates the vessel.

7. The method of claim 6 wherein said plurality of directional air lift pumps are affixed to the heat exchanger.

8. The method of claim 7 further comprising the step whereby the directional air lift pumps are oriented to simultaneously create an uplift current from the bottom of the vessel to the top of the vessel and a rotational current defined by the perimeter of the vessel as the outer boundary and the heat exchanger as the inner axis.

9. The method of claim 1 whereby nutrient concentration in the vessel controls the initiation of stationary phase of the culture.

10. The method of claim 1 further comprising the step of adjusting carbon dioxide levels in the vessel thereby increasing relative lipid concentrations.

11. The method of claim 10 wherein the carbon dioxide is introduced into the culture by said airlift pumps.

12. The method of claim 1 further comprising the step of exposing the algae in the vessel to artificial lighting at wavelengths between 450 and 475 nm and 530 to 675 nm.

13. The method of claim 12 wherein the lighting is selected from the group consisting of metal halide lights and high pressure sodium lights.

14. The method of claim 12 wherein the lighting is selected from the group consisting of light emitting diodes emitting at the wavelengths.

15. The method of claim 12 further comprising the step of selectively filtering out ambient light to preselected wavelengths required for algae growth thereby reducing heat absorbed by the culture in the vessel.

16. The method of claim 15 further comprising the step of suspending a heat barrier over the vessel wherein the heat barrier reduces the intensity of light reaching the culture.

17. The method of claim 1 wherein the step of harvesting further comprises extracting a lipid fraction from the microalgal culture.

\* \* \* \* \*